United States Patent
Mueller et al.

(10) Patent No.: US 9,365,026 B2
(45) Date of Patent: Jun. 14, 2016

(54) METHOD FOR MULTI-STAGE CONTROL AND MEASUREMENT OF OPAQUE WHITE

(71) Applicant: HEIDELBERGER DRUCKMASCHINEN AG, Heidelberg (DE)

(72) Inventors: Robert Mueller, Moerlenbach (DE); Manfred Schneider, Bad Rappenau (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 0 days.

(21) Appl. No.: 14/466,313

(22) Filed: Aug. 22, 2014

(65) Prior Publication Data
US 2015/0053102 A1    Feb. 26, 2015

(30) Foreign Application Priority Data
Aug. 23, 2013   (DE) .......................... 10 2013 014 154

(51) Int. Cl.
*B41F 33/00*    (2006.01)
*B41F 7/02*    (2006.01)

(52) U.S. Cl.
CPC ............. *B41F 7/025* (2013.01); *B41F 33/0045* (2013.01)

(58) Field of Classification Search
CPC ............. B41F 33/0063; B41F 33/0027; B41F 33/0036; B41F 33/0045; B41F 7/025
See application file for complete search history.

(56) References Cited

U.S. PATENT DOCUMENTS

| | | | |
|---|---|---|---|
| 7,000,544 B2 | 2/2006 | Riepenhoff | |
| 8,154,761 B2 | 4/2012 | Huber et al. | |
| 2005/0237318 A1* | 10/2005 | Inoue et al. | 345/207 |
| 2006/0214940 A1* | 9/2006 | Kinoshita et al. | 345/589 |
| 2007/0079717 A1* | 4/2007 | De Vries et al. | 101/484 |
| 2007/0201065 A1* | 8/2007 | Huber et al. | 358/1.9 |
| 2010/0110456 A1* | 5/2010 | Horita | 358/1.9 |
| 2011/0007318 A1* | 1/2011 | Okuda et al. | 356/433 |
| 2011/0116108 A1* | 5/2011 | Ha et al. | 358/1.2 |
| 2011/0219975 A1* | 9/2011 | Whitelaw | 101/483 |
| 2012/0012018 A1* | 1/2012 | Birecki et al. | 101/335 |

(Continued)

FOREIGN PATENT DOCUMENTS

| | | |
|---|---|---|
| DE | 3530561 A1 | 3/1987 |
| DE | 19724171 A1 | 10/1997 |
| DE | 10131934 A1 | 1/2003 |
| DE | 102005021185 A1 | 11/2005 |
| DE | 102007005018 A1 | 8/2007 |

(Continued)

*Primary Examiner* — David Banh
(74) *Attorney, Agent, or Firm* — Laurence A. Greenberg; Werner H. Stemer; Ralph E. Locher

(57) ABSTRACT

An ink control method is provided for printing machines having a computer. The color areas are scanned on a surface to be printed using a color measuring device. The surface is a printing substrate coated with opaque white, and the color measuring device takes a number of opaque white color measurements. The computer compares the measured opaque white color values to each other or to a reference color value of the opaque white and stores deviations detected in the computer. The color measurement fields are printed onto the printing substrate. The color measurement fields printed onto the opaque white are measured by the color measuring device. The comparison of the measured color values of the color measurement fields under laid with opaque white and the target color values of the original for color control purposes, the computer factors in the influence of the stored detected deviations.

10 Claims, 1 Drawing Sheet

(56) References Cited

U.S. PATENT DOCUMENTS

2012/0250095 A1 10/2012 Bestmann
2012/0287189 A1 11/2012 Shimada et al.

FOREIGN PATENT DOCUMENTS

DE 102007008849 A1 9/2007
DE 102011015306 A1 10/2012

* cited by examiner

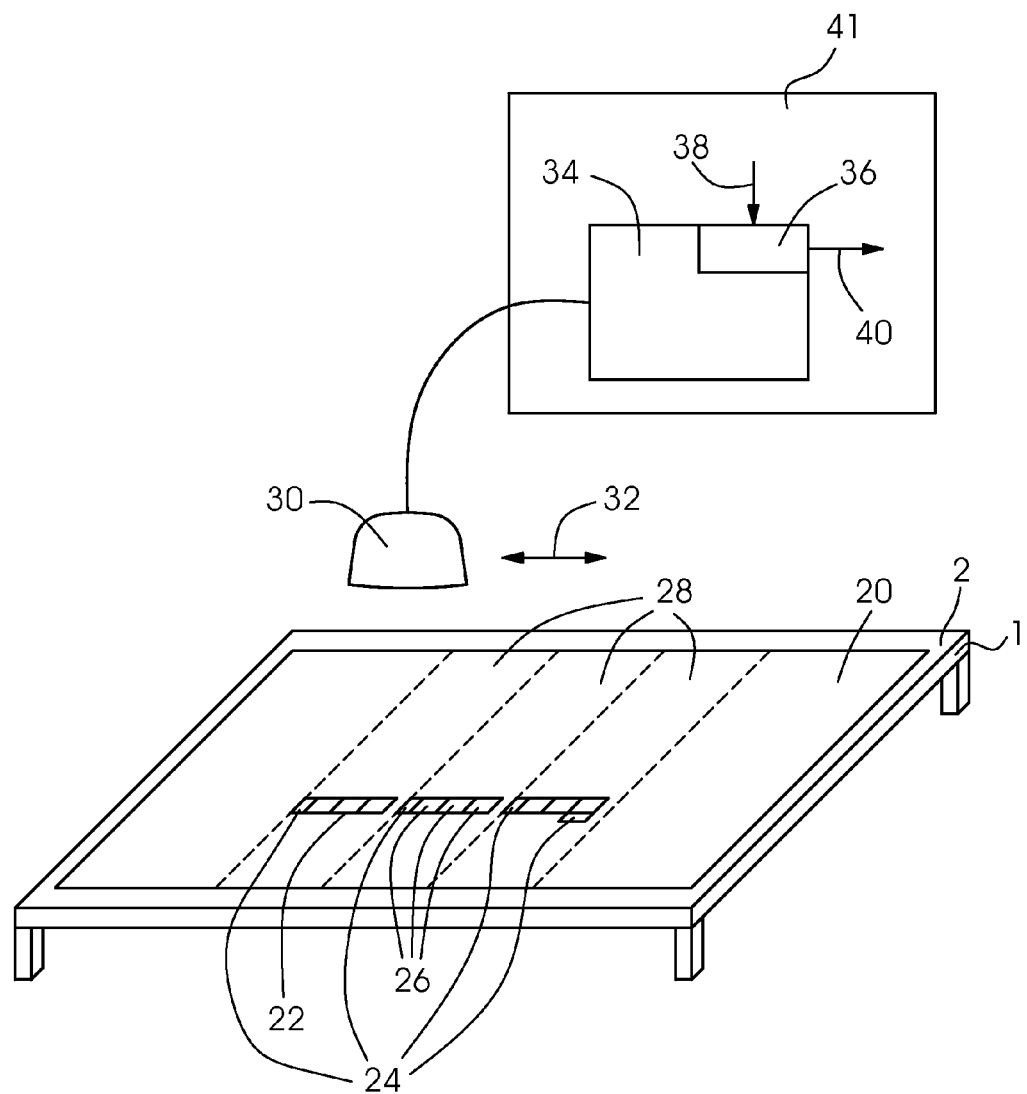

METHOD FOR MULTI-STAGE CONTROL AND MEASUREMENT OF OPAQUE WHITE

CROSS-REFERENCE TO RELATED APPLICATION

This application claims the priority, under 35 U.S.C. §119, of German application DE 10 2013 014 154.0, filed Aug. 23, 2013; the prior application is herewith incorporated by reference in its entirety.

BACKGROUND OF THE INVENTION

Field of the Invention

The invention relates to an ink control method for printing presses with a computer wherein color areas on a surface to be printed are measured by a color measuring device.

Spectral measurements on color measurement strips are a common and well-established method for color measurements of printing inks applied to a printing substrate. Prerequisites for such a measurement are that the printing substrate be brighter than the color to be printed and that the printing ink appears darker the thicker the applied ink film. The latter is the case where lithographic offset printing inks are concerned. In this context, people skilled in the art will be familiar with the color control systems for printing presses, in particular lithographic offset printing presses, marketed by Heidelberger Druckmaschinen AG under the trade names IMAGE CONTROL®, AXIS CONTROL® and/or INPRESS CONTROL®.

In the spectral measurement process, the thickness of the ink film is determined on the basis of a measured brightness difference between the printing substrate and the applied printing ink. Usually the printing substrate is a white sheet of paper. In this case, the afore-described spectral measurement works without difficulty because even a thin film appears darker than the white of the sheet. However, this does not always apply to darker printing substrates where the printing ink may appear brighter than the printing substrate. The same problem occurs in spectral color measurement processes carried out on metals or transparent foils. Metals have reflective properties and consequently appear black to a spectral measuring device, also known as a spectrophotometer, under standard conditions (measurement angle of 0 and 45 degrees, respectively). In spectral measurements on transparent foils, the surface on which the transparent foil is lying will always shine through. If the measurement is taken outside the machine, this will be the dark printing table; if the measurement is an in-line measurement, this will be a cylinder made of metal.

In practice, this problem may be circumvented by under laying the color measurement strip with opaque white to enable color measurements and color control measures within the color measurement strip. Yet to provide precise and accurate measurements for optimum printing ink control measures, the opaque white needs to be applied as evenly as possible. The under laying with opaque white is done manually, i.e. for instance in a printing unit that is provided upstream of those that apply the different-color inks and does not have automated color measurement and control devices. As a consequence, deviations will inevitably occur both between the individual measurement strips and between the ink zones of an individual measurement strip. These deviations will lead to different measured values, which will in turn translate into erroneous ink film thickness deviations of the printing ink because the assumption is made that the background is identical.

Another option to circumvent the difficulties described above implemented in practice is to provide an opaque-white halftone field of 70%, for example, in a color measurement strip. For the measurement process, the opaque white and the substrate switch places, i.e. the halftone field is examined as if the opaque white was the background and the substrate was the printing ink. This means that the tone value of a black halftone field, in this case 30% for example, is measured on a white printing substrate. Although this method allows to adapt multiple ink zones of a zonal printing press relative to each other and to detect fluctuations during operation, the opaque white itself needs to be measured using an external measurement device and not during operation. In addition, the method does not work with conventional color control systems because the control measure is in the wrong direction. This is due to the fact that for color printing inks, the colors turn darker as the thickness of the ink film increases whereas opaque white on a dark background gets brighter the thicker the ink film.

If the printing substrates are transparent, it is furthermore possible to place a white strip of paper, plastic or the like underneath the substrate. This option is not available for non-transparent printing substrates.

Published, non-prosecuted German patent application DE 10 2007 005 018 A1, corresponding to U.S. Pat. No. 8,154,761, discloses an ink control method for copies created in a printing press wherein printing ink that is brighter than the substrate is applied to a substrate that appears to be dark in a standardized color measurement and at least one color value of the printing ink is established from a measured value. The method is characterized by the fact that the color value of the at least one printing ink is controlled with the aid of a defined reference value of a color location that is brighter than the printing ink in the color space.

Published, non-published German patent application DE 197 24 171 A1 discloses an ink control method in printing presses wherein the inhomogeneities of the unprinted substrate are factored in as the colors are measured after printing. For this purpose, measurements are taken at a number of locations on the unprinted substrate to detect inhomogeneities such as contaminations on the unprinted sheet. Subsequently, measurements are taken on the printed substrate. The measured values of the printed substrate are than corrected on the basis of the measured values of the unprinted substrate to avoid any falsifying influence on the ink control measures caused by contaminations on the unprinted sheet.

SUMMARY OF THE INVENTION

It is accordingly an object of the invention to provide a method for multi-stage control and measurement of opaque white that overcomes the above-mentioned disadvantages of the prior art methods of this general type, which allows reliable ink control based on reliable spectral measurements for printing machines even when the printing inks are applied to surfaces that are darker than the applied inks or transparent.

In accordance with the ink control method of the invention, a color measuring device is used to take a number of color measurements on a surface that is to be printed on and has been coated with opaque white. The color measurements of the opaque white surface are compared to each other or to a reference color value of the opaque white in a computer. The deviations established by the comparison are stored in the computer. Then color measurement fields are printed onto the printing substrate that has been coated with opaque white. These measurement fields are in turn measured by the color measuring device. In the comparison for the purpose of controlling the inking of the color measurement fields underlaid with opaque white and the target values of the original, the deviations that have been detected and stored are factored in by the computer. With the aid of this embodiment, printing ink control measures are possible even on highly reflective or very dark surfaces.

In accordance with an alternative or additional embodiment of the invention, a number of color measurements of the opaque white are taken on the printing substrate by a color measuring device. The measured color values of the opaque white are then compared to each other or to a reference color value of opaque white by a computer. The deviations between the measured color values themselves or between the measured color values and the reference value of the opaque white as detected by the comparison are then corrected by the computer to obtain a common value. This method may be combined with the aforementioned correcting method, for example by controlling the opaque white in a first step and, after the controlling step, factoring in the still-existing deviations from the ideal opaque white as correction values for controlling the different color inks including black. Thus a parallel or sequential combination of the two methods is possible. In addition, opaque white and the different-color printing ink may be controlled in parallel or sequentially. For a parallel control, the effects on the printing ink of the changes to be expected in the opaque white during the step of controlling the opaque white need to be factored in for a simultaneous control of the colored inks. An advantage of the simultaneous control of the color inks and opaque white is that it saves material and time.

In accordance with an advantageous further embodiment of the invention, after the correction of the opaque white, the color measurement fields that have been under laid with opaque white are scanned by the color measuring device. A further expedient aspect of the invention is that the opaque white is measured in a color measurement strip including color measurement fields or adjacent to such a color measurement strip. Thus by adding an opaque white field, the color measurement strip required for color measurements is also used for the purpose of controlling the opaque white.

In accordance with a further expedient embodiment of the invention, the reference color value is either a stored predefined value, a stored print job value, or the brightest opaque white value across the entire width of the printing substrate.

In accordance with an advantageous further embodiment of the invention, the printing substrate is printed in ink zones and the color measuring device takes a measurement of opaque white and of the color measurement fields underlaid with opaque white in every ink zone or in every other ink zone on the printing substrate.

In accordance with an advantageous further embodiment of the invention, the reference color value for opaque white in an opaque condition is stored in a database and is accessed by the computer.

In accordance with a particularly advantageous embodiment of the invention, the computer displays the measured opaque white values on a display device and suggests the brightest measured opaque white value as a reference color value on the display device for confirmation by the operator.

In accordance with a particularly advantageous further embodiment of the invention, the first step in the color control process is to even out the opaque white on the printing substrate. Only then will the colors in the color measurement fields of the color measurement strip under laid with opaque white be controlled.

In accordance with an eminently advantageous further embodiment of the invention, the effects of the deviations of the opaque white on the measured color values of the color measurement fields under laid with opaque white are taken into consideration in the computer by taking into consideration color changes in the opaque white background in the form of spectrums in the computer and are taken into consideration in the computer for ink control purposes of the measured color values of the color measurement fields underlaid with opaque white. Alternatively, they may be factored in in the form of color density values or color coordinates.

Other features which are considered as characteristic for the invention are set forth in the appended claims.

Although the invention is illustrated and described herein as embodied in a method for multi-stage control and measurement of opaque white, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The single FIGURE of the drawing is a diagrammatic representation of an embodiment of a color measurement system according to the invention.

DETAILED DESCRIPTION OF THE INVENTION

Referring now to the single FIGURE of the drawing in detail, there is shown a diagrammatic representation of an embodiment of a color measurement system of the invention. A copy of a printing substrate 20 printed in a lithographic offset printing press has a color measurement strip 22. The color measurement strip 22 is under laid with opaque white 24. The color measurement strip has gaps for measuring the opaque white and contains measurement fields 26 for the other colors, in particular the standard process colors, in each ink zone 28. It is possible to provide measurement fields printed with opaque white in the color measurement strip 22 instead of the gaps. Opaque white and other colors may thus be measured and controlled in one measuring process. A measuring device 30 carries out a relative movement 32 with respect to the printing substrate 20 to take measurements of the measurement fields 26 and of the opaque white 24 in the color measurement strip 22 in the individual ink zones 28 for a closed-loop control device 34.

Initially a line of opaque white 24 is printed. The color values of the opaque white 24 measured by the color measuring device 30 in the various ink zones 28 are then compared to an opaque white reference color value in the computer 41. Then deviations of the measured opaque white color values from the opaque white reference color value are identified by the computer 41 and are corrected by the control device 34. Then the color measurement fields 26 are applied to the color measurement strip 22 that has hitherto only consisted of opaque white 24. At the same time, the printed image is printed outside the color measurement strip 22. Subsequently, the color measuring device 30 scans the color measurement fields 26 and a computer 41 compares the measured values to target values that are stored in the computer 41. Deviations between the color measurement fields 26 and the respective target color value are identified by the computer 41 and corrected by the control device 34.

The reference color value for controlling the opaque white is either a stored predefined value, a stored print job value, or the brightest measured opaque white value across the entire width of the printing substrate 20. The target or reference value is fed to a memory unit 36 of the control device 34 as a default specification. Then a signal 40 is output to the actuating elements of the lithographic offset printing press to control the opaque white 24 and the different-color inks in the color measurement strips 26 of the measurement strip 22 together with the printed image.

The following is a summary list of reference numerals and the corresponding structure used in the above description of the invention:

1 measurement table
2 measurement table surface
20 printing substrate
22 color measurement strip
24 opaque white surface
26 measurement fields in the color measurement strip
28 ink zone
30 color measuring device
32 relative movement
34 control device
36 memory unit
38 reference value specification
40 signal output for the actuating elements
41 control computer

The invention claimed is:

1. An ink control method for printing machines having a computer, which comprises the steps of:
   taking a number of color measurements of a surface of a printing substrate coated with opaque white by a color measuring device;
   comparing, via the computer, measured opaque white color values to each other or to a reference color value of the opaque white;
   storing deviations detected in a comparison in the computer;
   printing color measurement fields onto the printing substrate coated with the opaque white;
   measuring the color measurement fields printed onto the opaque white by the color measuring device; and
   comparing measured color values of the color measurement fields with target color values of an original, wherein, in the comparing of the measured color values of the color measurement fields under laid with the opaque white and the target color values of the original for color control purposes, the computer factors in an influence of stored detected deviations.

2. The method according to claim 1, wherein the computer additionally sequentially or in parallel compensates for the deviations of the measured opaque white color values from each other or from the reference color value of the opaque white.

3. The method according to claim 2, wherein after performing opaque white compensation, measuring the color measurement fields under laid with the opaque white via the color measuring device.

4. The method according to claim 1, which further comprises measuring the opaque white via the color measuring device in a color measurement strip with the color measurement fields or adjacent to the color measurement strip.

5. The method according to claim 1, wherein the reference color value of the opaque white is a stored predefined value, a stored print job value, or a brightest measured value of the opaque white across an entire width of the printing substrate.

6. The method according to claim 1, wherein the printing substrate is printed in ink zones and the color measuring device takes a measurement of the opaque white and of the color measurement fields under laid with the opaque white in every ink zone or in every other ink zone on the printing substrate.

7. The method according to claim 1, which further comprises storing the reference color value of the opaque white in an opaque condition in a database and accessed by the computer.

8. The method according to claim 5, which further comprises displaying, via the computer, the measured opaque white values on a display device and suggesting a brightest measured value of the opaque white as the reference color value on the display device for confirmation by an operator.

9. The method according to claim 2, wherein the opaque white on the printing substrate is evened out and then colors in the color measurement fields of the color measurement strip under laid with the opaque white are controlled.

10. The method according to claim 1, wherein effects of the deviations of the opaque white on the measured color values of the color measurement fields under laid with the opaque white are taken into consideration by the computer via recording and saving of color changes in an opaque white background in a form of spectrums and then using stored spectrums by the computer for ink control purposes of the measured color values of the color measurement fields under laid with the opaque white in the computer.

* * * * *